United States Patent
Karmazyn et al.

(10) Patent No.: US 9,889,280 B2
(45) Date of Patent: Feb. 13, 2018

(54) RECTAL CATHETER CONFIGURED FOR PEDIATRIC CARE

(71) Applicant: Indiana University Research and Technology Corporation, Indianapolis, IN (US)

(72) Inventors: Boaz Karmazyn, Indianapolis, IN (US); Megan Marine, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 667 days.

(21) Appl. No.: 14/242,080

(22) Filed: Apr. 1, 2014

(65) Prior Publication Data

US 2014/0296832 A1    Oct. 2, 2014

Related U.S. Application Data

(60) Provisional application No. 61/807,136, filed on Apr. 1, 2013.

(51) Int. Cl.
| | |
|---|---|
| *A61M 25/10* | (2013.01) |
| *A61M 31/00* | (2006.01) |
| *A61F 2/00* | (2006.01) |
| A61M 25/02 | (2006.01) |

(52) U.S. Cl.
CPC ..... *A61M 25/10185* (2013.11); *A61F 2/0004* (2013.01); *A61F 2/0009* (2013.01); *A61F 2/0013* (2013.01); *A61M 31/00* (2013.01); *A61M 31/005* (2013.01); *A61M 2025/0233* (2013.01)

(58) Field of Classification Search
CPC ............ A61M 25/10185; A61M 31/00; A61M 2025/0233; A61F 2/0004; A61F 2/0009; A61F 2/0013
See application file for complete search history.

(56) References Cited

U.S. PATENT DOCUMENTS

| | | |
|---|---|---|
| 3,802,418 A * | 4/1974 | Clayton ............ A61M 25/1009 600/562 |
| 4,686,985 A | 8/1987 | Lottick |
| 6,096,057 A | 8/2000 | Klingenstein |
| 6,575,932 B1 | 6/2003 | O'Brien et al. |
| 7,360,544 B2 | 4/2008 | Levien |
| 8,016,816 B2 | 9/2011 | Gregory |

(Continued)

*Primary Examiner* — Nathan R Price
*Assistant Examiner* — Anh Bui
(74) *Attorney, Agent, or Firm* — Faegre Baker Daniels LLP

(57) ABSTRACT

A rectal catheter is configured for improved pediatric care. The catheter includes a member that terminates into a rounded tip, a plug mounted about the member, the plug being made of a moldable material, a balloon mounted about the member between the rounded tip and the plug, a conduit that fluidly communicates with the balloon and that extends from the member to enable a pressure source to be operatively connected to the balloon to inflate the balloon, and a pressure relief valve operatively connected to the conduit, the pressure relief valve being configured to open the conduit to atmosphere pressure in response to a pressure in the conduit reaching a predetermined pressure. The predetermined pressure is selected to attenuate significantly risk of bowel perforation in pediatric patients.

18 Claims, 2 Drawing Sheets

(56) References Cited

U.S. PATENT DOCUMENTS

| | | | |
|---|---|---|---|
| 2004/0106899 A1* | 6/2004 | McMichael | A61J 15/0015 |
| | | | 604/104 |
| 2007/0149922 A1* | 6/2007 | Schneider | A61M 16/0434 |
| | | | 604/99.01 |
| 2010/0234821 A1 | 9/2010 | Bjerregaard et al. | |
| 2011/0082444 A1 | 4/2011 | Mayback et al. | |

* cited by examiner

RECTAL CATHETER CONFIGURED FOR PEDIATRIC CARE

CLAIM OF PRIORITY

This document is a utility patent application that claims priority to U.S. provisional patent application Ser. No. 61/807,136, which is entitled "A Rectal Catheter Configured For Pediatric Care" and was filed on Apr. 1, 2013, which is expressly incorporated in this document in its entirety by reference.

TECHNICAL FIELD

The device disclosed in this document relates to rectal catheters, and, more particularly, to rectal catheters used in pediatric care.

BACKGROUND

Current techniques used in conducting enema studies in pediatric patients, such as, but not necessarily limited to, ileocolic intussusception reduction and treatment of meconium ileum, typically are conducted with a simple rectal catheter. These simple catheters require a significant amount of external adhesive tape to secure the catheter in place. Despite the adhesive tape tightly holding the buttocks together, a significant leakage of air or fluid from the anus can occur during the exam. This leakage can result in decreased effectiveness of the procedure, discomfort to the patient, increased radiation, and increased time for the procedure. The use of rectal catheters in children is also complicated by the length of the anal canal, which varies with patient age and ranges from 2 cm to 4 cm. Rectal catheters having balloons that are inflated within a patient's rectum to block fluid passage in adult patients present a significant risk for rectal perforation in the pediatric population. A survey conducted by the Society of Pediatric Radiology attests to instances of rectal perforation occurring during enema studies for meconium ileus conducted with such balloon-tip catheters. What is needed is a rectal catheter that attenuates the risk of rectal catheter use with pediatric patients.

SUMMARY

A disposable, leak resistant pediatric rectal catheter has been configured with an inflatable, internal pressure-controlled rectal balloon to address issues related to lower bowel treatment in pediatric patients. The catheter includes a member that terminates into a rounded tip, a plug mounted about the member, the plug being made of a moldable material, a balloon mounted about the member between the rounded tip and the plug, a conduit that fluidly communicates with the balloon and that extends from the member to enable a pressure source to be operatively connected to the balloon to inflate the balloon, and a pressure relief valve operatively connected to the conduit, the pressure relief valve being configured to open the conduit to atmosphere pressure in response to a pressure in the conduit reaching a predetermined pressure. The predetermined pressure is selected to attenuate significantly risk of bowel perforation in pediatric patients.

DETAILED DESCRIPTION

Figure 1:
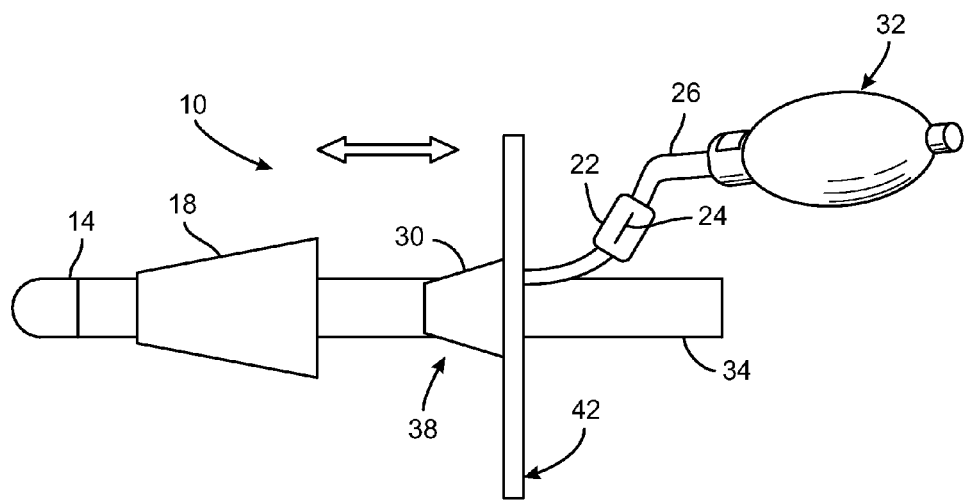
FIG. 1 depicts a rectal catheter configured for use with a range of pediatric patients.

FIG. 1 shows a disposable, leak resistant pediatric rectal catheter 10 that is configured for use with pediatric patients. The catheter 10 has a catheter body 34 having one or more lumens through the body. The body 34 terminates into a distal rounded tip 14. The tip 14 is made of a material that is sufficiently rigid to facilitate insertion of the catheter body 34 into a patient without presenting an unreasonable risk of bowel perforation or discomfort. An inflatable, internal pressure-controlled rectal balloon 18 is fixedly mounted about the catheter body 34 at a predetermined distance from the tip 14. The predetermined distance is less than 2 cm to enable the balloon to be fully inserted into the shortest anal canal typically encountered in pediatric health care. The balloon 18 fluidly communicates with a pressure source 32 through a balloon inflation conduit 26. The pressure source 32 is depicted as a pressure bulb and pressure gauge, such as can be found on a sphygmomanometer, although other pressure sources, such as pump or syringe can be used as well. The conduit 26 enters the catheter body 34 at a position that remains external to the patient's body. The pressure source 32 provides a gas or liquid to expand the balloon, which fills space within the bowel to prevent leakage of liquid from the rectum. Another lumen can be provided in the catheter body 34. This lumen can have an opening between the tip 14 and the balloon 18 to enable removal of fluids from the rectum or to administer contrast or therapeutic agents to the rectum.

The rectal balloon 18 has an attached safety pressure release valve 22 that fluidly communicates with the lumen of the balloon inflation conduit 26 to ensure the balloon is not inflated above 40 mmHg, which is well below the stated mean pressure of 108 mmHg noted in the literature that documents bowel perforations in pediatric care. The valve may be a slit 24 in the side of the conduit 26. The slit 24 is formed in a manner that enables the slit to open to the atmosphere at a predetermined pressure in the conduit 26 so the fluid or gas exits the conduit. This structure prevents the pressure in the conduit 26 from exceeding the predetermined pressure. Alternatively, the pressure relief valve can be a mechanical pressure relief valve, such as the valve 52 shown in FIG. 2, that communicates with the lumen in the conduit 26 to perform a pressure relieving function similar to the one described with reference to the slit.

The catheter 10 also includes a sliding adjustable, moldable external stopper 38. The stopper 38 includes a conical plug 30 and a planar disc 42 mounted abut a portion of the catheter body 34 that remains external to the patient's body. The stopper 38 slides with reference to the catheter body 34 so the distance between the distal tip 14 and the plug 30 of the stopper 38 can be adjusted to accommodate different anal canal lengths. The conical plug 30 is made of a fluid resilient and moldable material that can be inserted into the anus and conformed to the anus opening. The disc 42 has a circular shape and the circumference of the disc has a gripping surface to enable the medical personnel manipulating the stopper 38 to maintain control of the plug 30 as the plug 30 is slid into the anus to a position appropriate for preventing leakage and improving a seal at the anus. Additionally, the planar surface of the disc 42 provides a flat surface to which adhesive tape can be applied. The planar surface of the disc 42 has an adequate area to enable the tape to remain in place on the disc to help hold the plug 30 at the appropriate position in the anus.

Figure 2:
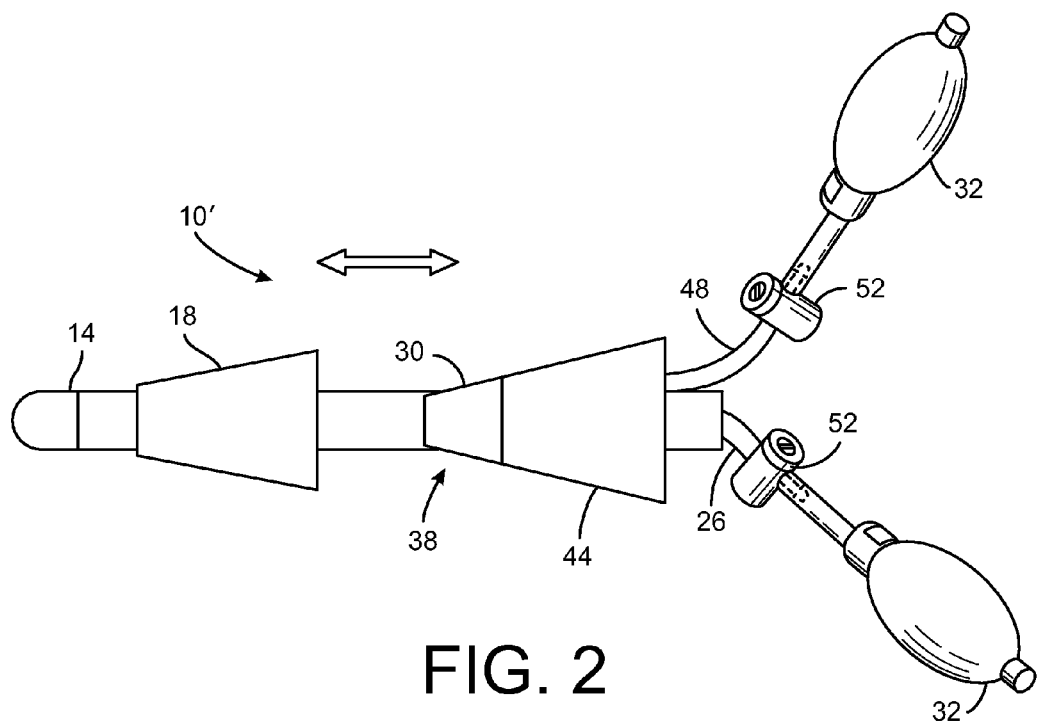
FIG. 2 depicts an alternative embodiment of the rectal catheter shown in FIG. 1.

Using like numbers for like structures, an alternative embodiment 10' of the catheter shown in FIG. 1 is depicted in FIG. 2. This alternative embodiment differs from the embodiment shown in FIG. 1 in that the stopper 38 includes the conical plug 30 and a second balloon 44, which replaces the external disc 42. The balloon 44 has an internal volume that is fluidly connected to a lumen of a second balloon inflation conduit 48, which in turn is fluidly connected to a pneumatic pressure source. Two mechanical safety pressure release valves 52 are provided in embodiment 10'. One mechanical pressure valve 52 fluidly communicates with the lumen of the balloon inflation conduit 26, which inflates/deflates the balloon 18. This valve helps ensure the balloon 18 is not inflated above 40 mmHg, which is well below the stated mean pressure of 108 mmHg noted in the literature that documents bowel perforations in pediatric care. As noted above, this valve may be a slit in the side of the conduit 48. In such an embodiment, the slit is formed in a manner that enables the slit to open to the atmosphere at a predetermined pressure in the conduit 48 so the fluid or gas exits the conduit. This structure prevents the pressure in the conduit 48 from exceeding the predetermined pressure. The other mechanical pressure relief valve 52 fluidly communicates with the lumen in the conduit 48 to perform a pressure relieving function similar to the one described with reference to the slit. This valve may be set to the same or a different pressure than the valve 52 that communicates with lumen 26.

Figure 3:
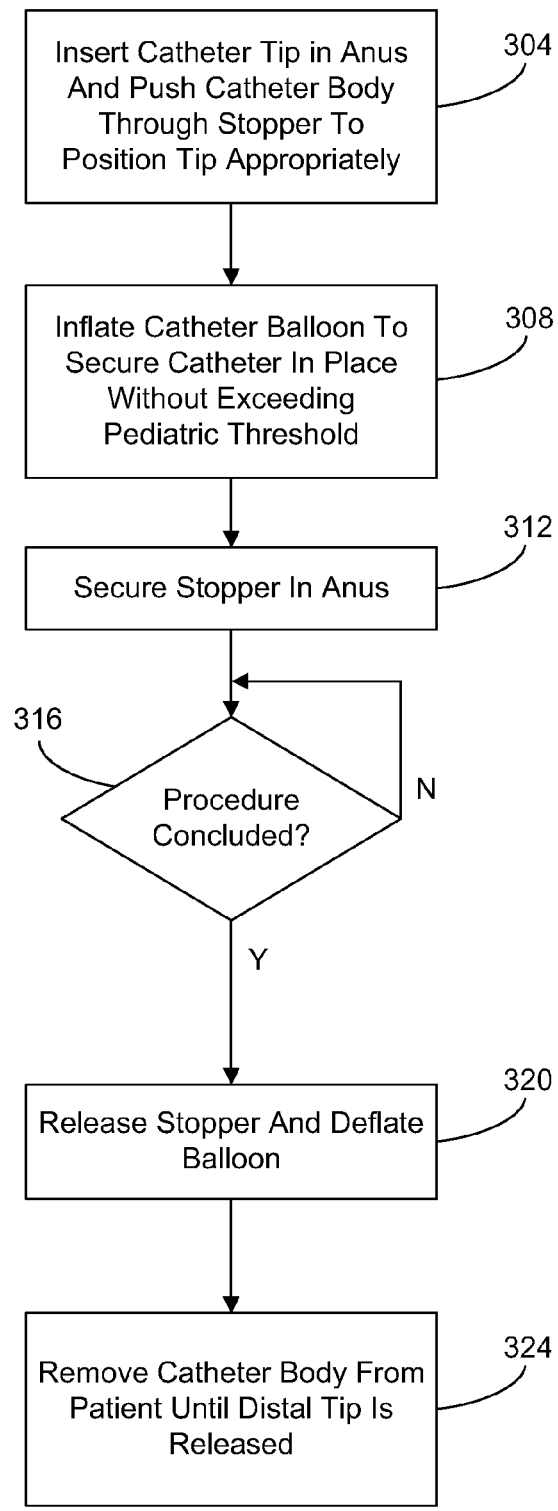
FIG. 3 is a flow diagram for a procedure using the pediatric rectal catheter.

A procedure for using the pediatric rectal catheter described above is shown in FIG. 3. That process commences with the distal tip 14 being inserted into the anus and the catheter body 34 is pushed through the stopper 38 to position the tip 14 at an appropriate position for the pediatric patient (block 304). As the catheter body 34 enters the anal canal, it carries balloon 18 with it. When the tip 14 is at the appropriate position, a pressure source is activated to supply pneumatic pressure into balloon 18 to inflate the balloon to a pressure adequate to hold the tip 14 at the appropriate position without exceeding the 40 mm Hg maximum (block 308). The stopper is then secured in the anus (block 312). In one embodiment, the stopper is secured by gripping the disc 42 of the stopper 38 and sliding the stopper 38 about the catheter body 34 to urge the plug 30 into the anus. When the plug is at a position that adequately prevents leakage from the anus, a portion of a length of adhesive tape is applied to the planar surface of the disc 42 and the ends of the tape length are secured to the patient to hold the stopper 38 in position. In the alternative embodiment, the stopper is secured by applying force to the rear of the plug 30 to move the plug 30 into position to seal the anus, while the balloon 44 remains deflated. The balloon 44 follows the plug and enters the anus. Balloon 44 is then inflated to a size that secures the balloon within the anus and holds the plug 30 of the stopper 38 at the position where the plug 30 seals the anus. The catheter remains in position until the procedure being conducted on the pediatric patient is concluded (block 316). Once the procedure is completed, the stopper is released and the balloon deflated (block 320). The catheter body 34 is then removed from the patient until the distal end exits the patient (block 324).

The reader should appreciate that variants of the above-disclosed and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following claims.

What is claimed:

1. A rectal catheter comprising:
   a member that terminates into a rounded tip;
   a plug made of moldable material, the plug being mounted about the member and configured for bi-directional sliding along the member;
   a disc mounted to the plug, the plug being positioned between the disc and the rounded tip;
   a balloon fixedly mounted about the member at a predetermined position that is between the rounded tip and the plug;
   a conduit that fluidly communicates with the balloon and that extends from the member to enable a pressure source to be operatively connected to the balloon to inflate the balloon; and
   a pressure relief valve operatively connected to the conduit, the pressure relief valve being configured to open the conduit to atmosphere pressure in response to a pressure in the conduit reaching a predetermined pressure, wherein the plug includes a first end proximate the balloon and a second end proximate the disc, the plug being tapered at a constant slope between the first end and the second end.

2. The rectal catheter of claim 1 wherein the disc has a circular shape.

3. The rectal catheter of claim 2, the disc further comprising:
   a gripping surface on a circumference of the disc.

4. The rectal catheter of claim 1 wherein the disc has a planar surface.

5. The rectal catheter of claim 1 wherein the plug has a conical shape.

6. The rectal catheter of claim 1, the pressure relief valve further comprising:
   a slit in the conduit that is configured to open to atmospheric pressure at the predetermined pressure.

7. The rectal catheter of claim 1, the pressure relief valve further comprising:
   a mechanical pressure relief valve that communicates with a lumen in the conduit and that opens to atmospheric pressure at the predetermined pressure.

8. The rectal catheter of claim 1 wherein the predetermined pressure is less than 50 mm Hg.

9. The rectal catheter of claim 1 wherein the predetermined position at which the balloon is mounted to the member is located no more than 2 cm from the rounded tip.

10. A rectal catheter comprising:
    a member that terminates into a rounded tip;
    a conical plug made of moldable material, the conical plug being mounted about the member and configured for bi-directional sliding along the member, wherein a first end of the conical plug is a first width and a second end of the conical plug is a second width, the first width being less than the second width, and the conical plug being tapered at a constant slope between the first end and the second end;
    a balloon fixedly mounted about the member at a predetermined position that is between the rounded tip and the conical plug;
    a conduit that fluidly communicates with the balloon and that extends from the member to enable a pressure source to be operatively connected to the balloon to inflate the balloon;

and a pressure relief valve operatively connected to the conduit, the pressure relief valve being configured to open the conduit to atmosphere pressure in response to a pressure in the conduit reaching a predetermined pressure that is less than 50 mm Hg.

11. The rectal catheter of claim 10 further comprising:
a circular disc mounted to the conical plug, a circumference of the disc having a gripping surface.

12. The rectal catheter of claim 11 wherein the circular disc has a planar surface.

13. The rectal catheter of claim 10, the pressure relief valve further comprising:
a slit in the conduit that is configured to open to atmospheric pressure at the predetermined pressure.

14. The rectal catheter of claim 10, the pressure relief valve further comprising:
a mechanical pressure relief valve that communicates with a lumen in the conduit and that opens to atmospheric pressure at the predetermined pressure.

15. The rectal catheter of claim 10 wherein the predetermined position at which the balloon is mounted to the member is located no more than 2 cm from the rounded tip.

16. The rectal catheter of claim 10 further comprising:
another balloon fixedly mounted to the conical plug;
a conduit that fluidly communicates with the other balloon and that extends from the other balloon to enable a pressure source to be operatively connected to the other balloon to inflate the other balloon; and
a pressure relief valve operatively connected to the conduit, the pressure relief valve being configured to open the conduit to atmosphere pressure in response to a pressure in the conduit reaching a predetermined pressure.

17. A method of using a rectal catheter with a pediatric patient comprising:
inserting a distal end of a catheter body into an anal canal of a pediatric patient to a predetermined position, wherein a conical plug mounted about the catheter body is configured to seal the anal canal in the predetermined position;
inflating a catheter balloon positioned on the catheter body and located within the anal canal of the pediatric patient to secure the catheter balloon, a portion of the catheter body, and the distal end within the anal canal;
releasing pressure from the inflated balloon in response to the pressure within the balloon exceeding 40 mm Hg;
deflating the balloon in response to a procedure on the pediatric patient being completed; and
removing the catheter balloon, catheter body, and distal end from the pediatric patient, wherein the conical plug includes a first end proximate the catheter balloon and a second end opposite the first end, the conical plug being tapered at a constant slope between the first end and the second end.

18. The rectal catheter of claim 1, wherein the plug is configured to seal an anus of a patient.

* * * * *